United States Patent [19]

Lewis et al.

[11] Patent Number: 4,659,728

[45] Date of Patent: Apr. 21, 1987

[54] HYDROXY SUBSTITUTED 4,5-DIPHENYL-2-OXAZOLE PROPANOIC ACID

[75] Inventors: Alan J. Lewis, Audubon; Richard P. Carlson, Lansdale; Horace Fletcher, 3rd, Pottstown, all of Pa.

[73] Assignee: American Home Products Corporation, New York, N.Y.

[21] Appl. No.: 704,824

[22] Filed: Feb. 25, 1985

[51] Int. Cl.⁴ .................... C07D 263/44; A61K 31/42
[52] U.S. Cl. .................................... 514/374; 548/236
[58] Field of Search .................... 548/236; 514/374

[56] References Cited

U.S. PATENT DOCUMENTS 3,578,671  5/1971  Brown ............................... 260/307

OTHER PUBLICATIONS

Fujioka et al, Chem. Abst. 100-185253j.
Abe et al, Chem. Abst. 101-122711g.
Janssen et al., Drug Metabolism and Disposition 6 (No. 4), 465 (1978).

*Primary Examiner*—Donald G. Daus
*Assistant Examiner*—C. Shen
*Attorney, Agent, or Firm*—Richard K. Jackson

[57] ABSTRACT

This invention discloses 5-(4-hydroxyphenyl)-4-phenyl-2-oxazolepropanoic acid, 4-(4-hydroxyphenyl-5-phenyl-2-oxazolepropanoic acid and pharmaceutically acceptable salts thereof as antiinflammatory agents, pharmaceutical compositions thereof and methods for their use.

5 Claims, No Drawings

HYDROXY SUBSTITUTED 4,5-DIPHENYL-2-OXAZOLE PROPANOIC ACID

BACKGROUND OF THE INVENTION

Oxaprozin (4,5-diphenyl-2-oxazolepropanoic acid) is a nonsteroidal antiinflammatory agent which also possesses antipyretic, uricosuric and immunologic properties. It is believed, like other nonsteroidal antiinflammatory agents of the propionic acid type, that oxaprozin functions as a prostaglandin biosynthesis inhibitor.

The metabolism of oxaprozin (U.S. Pat. No. 3,578,671) was studied by Janssen et al., Drug Metabolism and Disposition, 6 (No. 4), 465 (1978), who found two major metabolites which were denominated metabolites II and III. Metabolite III was identified as 4-(4-hydroxyphenyl)-5-phenyl-2-oxazolepropanoic acid by preparation of its 4-methoxyphenyl ether and comparison with a known sample of 4-(4-methoxyphenyl)-5-phenyl-2-oxazolepropanoic acid prepared in U.S. Pat. No. 3,578,671. The structure of metabolite II was not further elucidated than to identify the presence of an aromatic hydroxy group.

DESCRIPTION OF THE INVENTION

It has now been discovered that the identity of metabolite II of oxaprozin, as reported by Janssen et al., is in fact 5-(4-hydroxyphenyl)-4-phenyl-2-oxazolepropanoic acid. Furthermore, it has now been discovered that both of the major metabolites of oxaprozin—4-(4-hydroxyphenyl)-5-phenyl-2-oxazolepropanoic acid and 5-(4-hydroxyphenyl)-4-phenyl-2-oxazolepropanoic acid and pharmaceutically acceptable salts thereof are as effective as oxaprozin in inhibiting inflammation.

Thus, in accordance with this invention there is provided a novel organic chemical compound, namely 5-(4-hydroxyphenyl)-4-phenyl-2-oxazolepropanoic acid and pharmaceutically acceptable salts thereof. In addition, this invention provides pharmaceutical compositions containing the antiinflammatory agents, 5-(4-hydroxyphenyl)-4-phenyl-2-oxazolepropanoic acid and 4-(4-hydroxyphenyl)-5-phenyl-2-oxazolepropanoic acid or pharmaceutically acceptable salts thereof, as well as methods for using these pharmaceutical compositions of matter in treatment of rheumatoid arthritis, osteoarthritis, juvenile rheumatoid arthritis, ankylosing spondylitis, acute tendonitis/bursitis, acute gout and similar disease states attended by tissue inflammation, in the same manner as oxaprozin is employed.

The pharmaceutical salts of the antiinflammatory agents of this invention include acid addition salts of the basic ring nitrogen atom or a salt of the free carboxyl group. Applicable acid addition salts include those derived from such acids as hydrochloric, hydrobromic, sulfuric, phosphoric, methanesulfonic, nitric, p-toluene sulfonic, acetic, citric, maleic, succinic acid and the like. The carboxylic acid salts include alkali metal (sodium or potassium), alkaline earth metal (calcium or magnesium), ammonium or primary, secondary and tertiary alkylamines, the latter containing from 1 to 6 carbon atoms in their alkyl moieties. These salts are prepared by conventional means as desired.

The pharmaceutical compositions comprise an antiinflammatory amount of the herein described metabolites of oxaprozin and a non-toxic, pharmaceutically acceptable carrier. The pharmaceutically acceptable carrier of the antiinflammatory agents of this invention can be a solid or a sterile liquid. Applicable solid form compositions include powders, tablets and capsules for oral administration. The carrier may contain one or more substances including flavoring agents, lubricants, solubilizers, suspending agents, binders or disintegrants conventionally employed in the production of tablets or capsules. The solid dosage forms disclosed in U.S. Pat. No. 4,465,838 for calcium oxaprozin are applicable by substitution of the metabolites disclosed herein and the disclosure of that patent is incorporated herein by reference for that purpose.

Sterile liquid composition forms include solutions, suspensions, emuslions, syrups and elixirs. The antiinflammatory agent may be dissolved or suspended in the pharmaceutically acceptable sterile liquid carrier such as sterile water, sterile organic solvent or a mixture of the two solvents. Preferably the liquid carrier is suitable for parenteral administration such as isotonic water for injection, aqueous propylene glycol or polyethyleneglycol. Aqueous propylene glycol containing from 10 to 75 percent of the glycol by weight is generally suitable. The quantity of the antiinflammatory agents in these pharmaceutical compositions is substantially the same as that used with oxaprozin.

The antiinflammatory agents of this invention in either free acid or pharmaceutically acceptable salt form reduce inflammation in the mammal when administered neat or in pharmaceutically acceptable composition form, orally or parenterally, in an effective antiinflammatory amount, to a mammal in need thereof.

The antiinflammatory utility of the compounds of this invention was established by standard procedures for evaluating antiinflammatory agents, namely, carrageenan paw edema in the rat and adjuvant arthritis (polyarthritis) in the rat. These procedures and the results obtained are summarized below:

RAT CARRAGEENAN EDEMA

Groups of 6 male Sprague-Dawley rats (Honey Brook), weighing between 140–160 g were used in these experiments. Drugs were administered p.o. in 0.5% methylcellulose (400 centipoise). One hour after administering drugs or vehicle, 0.1 ml of 1% carrageenan was injected subplantar into the right hind paw. Right paw volumes were measured prior to carrageenan injection in milliliters using a mercury plethysmograph (i.e., zero time reading). After 3 hours, right paw volumes were remeasured and paw edema was calculated for each rat by subtracting the zero time reading from the 3 hour reading. Percent change in paw edema was calculated.

TABLE 1

| Treatment | Oral Dose (mg/kg) | % Inhibition of control paw edema |
|---|---|---|
| Oxaprozin | 200 | 51* |
| Example 1 Product | 150 | 43* |
| Example 2 Product | 150 | 46* |

*$p \leq 0.01$ from control

RAT ADJUVANT ARTHRITIS

Groups of 10 male Lewis rats (Charles River), weighing between 150–170 g were injected s.c. into the right paw with desiccated Mycobacterium butyricum (0.5 mg/0.1 ml) suspended in light mineral oil. Drugs were administered orally in 0.5% methylcellulose. The following dosing regimen was used: days 0 to 15 except for weekends. Both hind paw volumes, in milliliters, were measured by mercury plethysmography at the time of injection of the complete adjuvant (day 0). Paw volumes were measured on day 4 (injected paw only) and on day 16 (uninjected paw). Drug effects were expressed as percentage change from arthritic controls.

TABLE 2

| Treatment | Oral Dose (mg/kg) | % Inhibition of control uninjected paw edema at day 16 |
|---|---|---|
| Oxaprozin | 150 | 25* |
| Example 1 Product | 150 | 36* |
| Example 2 Product | 150 | 30* |

*$p \leq 0.01$ from control

Based upon the activity profile elicited by the compounds of this invention in the above-described standard scientifically recognized test model, the compounds are established as antiinflammatory agents useful in the treatment of inflammatory conditions in the mammal. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established to be substantially the same as oxaprozin, to be administered in single or plural doses as needed to relieve the inflammatory state. The specific dosage regimen for a given patient will depend upon age, pathological state, severity of dysfunction, size of the patient, etc. In unit dosage form, from about 100 to about 800 milligrams, preferably 200 to 750 milligrams and, more preferably from about 400 to 750 milligrams, of active ingredient is present.

The following examples are presented to illustrate the preparation of the antiinflammatory agents of the invention.

EXAMPLE 1

5-(4-hydroxyphenyl)-4-phenyl-2-oxazolepropanoic acid

4′-Methoxybenzoin (17.4 g, 0.0716 m) prepared according to R. T. Arnold and R. C. Fuson, J.A.C.S., 58, 1295 (1936), succinic anhydride (8.7 g, 0.086 m), triethylamine (3.541, 0.025 m) and toluene (30 ml) were heated on a steam cone under nitrogen for 2.5 hours. Thin layer chromatography (silica gel 60, ethyl acetate) showed complete conversion of the starting benzoin. Glacial acetic acid (40 ml) and ammonium acetate (7.6 g) were added and 40 ml of solvent were removed by distillation over 1 hour. Glacial acetic acid (40 ml) was added and 40 ml solvent removed by distillation. Glacial acetic acid (40 ml) was added and again 40 ml solvent removed by distillation. The cooled mixture was poured into 600 ml of ice water and the solid product was filtered. The product was purified by chromatography on a silica gel column using gradient elution from 100% chloroform to 90% chloroform:10% ethylacetate. Crystallization of the residue (29 g) from 200 ml of 50% aq. methanol gave 22.5 g of 5-(4-methoxyphenyl)-4-phenyl-2-oxazolepropanoic acid, m.p. 123°-126° C.

IR 1715 cm$^{-1}$, (shoulder at 1690 cm$^{-1}$).

$^1$H NMR (CDCl$_3$) δ2.99-3.2 (2d, 4H, —CH$_2$—CH$_2$), δ3.85 (S, 3H, —OCH$_3$), δ7.0-7.85 (m, 9H, arom.), δ9.25 (S, 1H, —COOH, D$_2$O exchangeable).

R$_f$ 0.50 silica gel 60 F254 chloroform:methylisobutylketone:acetic acid 50:50:1 A mixed melting point run with an authentic sample of the methyl ether of 4-(4-hydroxyphenyl)-5-phenyl-2-oxazolepropanoic acid (obtained from the metabolite of oxaprozin as disclosed by Janssen et al., Drug Metabolism and Disposition, 6, 495 (1978)), gave m.p. 92°-108° C., clearly demonstrating the lack of identity with the known metabolite. This, coupled with the identity of the 4′-methoxybenzoin starting material characterized the methyl ether as 5-(4-methoxy)-4-phenyl-2-oxazolepropanoic acid.

5-(4-methoxyphenyl)-4-phenyl-2-oxazolepropanoic acid (18.5 g, 0.056 m) dissolved in 700 ml dichloromethane was treated with boron tribromide (275 ml of 1M in dichloromethane) at 25° C. for twenty hours. The solution was poured into 1 l of ice and water and extracted with 2×500 ml of diethyl ether. The organic extracts were washed with water and extracted with 2×500 ml 1N sodium hydroxide. The basic aqueous solution was acidified with 12N hydrochloric acid to pH 2 and extracted with diethyl ether. The ether solution was washed with brine, dried over anhydrous MgSO$_4$ and evaporated. Thin layer chromatography on silica gel 60 with methylisobutylketone:CHCl$_3$:acetic acid 50:50:1 revealed two products detectable with U.V. and Bray's phenol spray. Comparative TLC demonstrated that the less polar product corresponded to metabolite II and the more polar product corresponded to metabolite III of Janssen et al. The two products were separated by HPLC on silica gel with methylene chloride:ethyl acetate:acetic acid 80:20:1. The appropriate fractions were pooled and evaporated. 9.0 Grams of the title and major product were obtained which were crystallized from 100 ml of hot ethyl acetate by chilling. Yield: 5.1 g, m.p. 175°-176°.

IR 1700 cm$^{-1}$ strong., 2000-3500 cm$^{-1}$ wide.

$^1$H NMR (DMSO) δ2.75-3.0 (2d, 4H), δ6.7 (s, 1H), δ6.85 (s, 1H), δ7.3-7.7 (m, 7H), δ9.75 (s, 1H exchangeable).

R$_f$ 0.60 silica gel 60 F254 CHCl$_3$:methylisobutylketone:acetic acid 50:50:1.

Analysis for: C$_{18}$H$_{15}$NO$_4$ Calculated: C, 69.89; H, 4.89; N, 4.53. Found: C, 69.97; H, 5.01; N, 4.48.

EXAMPLE 2

4-(4-Hydroxyphenyl)-5-phenyl-2-oxazolepropanoic acid

4-Methoxybenzoin (24 g, 0.1 m) prepared according to B. R. Kinney, J.A.C.S., 51, 1595 (1929), succinic anhydride (12 g, 0.12 m), triethylamine (5 ml, 0.035 m) and toluene (30 ml) were heated on a steam cone for three hours under nitrogen. After cooling, acetic acid (60 ml) and ammonium acetate (10.5 g) were added and heating was resumed as 60 ml of solvent were distilled. Acetic acid (30 ml) was added and 30 ml of solvent were distilled. The previous step was repeated twice more. The mixture was cooled and poured into 600 ml of ice water, decanted, triturated twice with ice water and filtered. Recrystallization from 50% aqueous methanol gave 24.2 g, (71%) of 4-(4-methoxyphenyl-5-phenyl-2-oxazolepropanoic acid, m.p. 118°-120° C.

IR 1690 cm$^{-1}$, 1720 cm$^{-1}$.

$^1$H NMR (CDCl$_3$) δ2.75-3.1 (2d, 4H, —CH$_2$CH$_2$—), δ3.72 (s, 3H, —OCH$_3$), δ6.3-7.6 (m, 9H, arom.), δ10.6 (s, 1H, D$_2$O exchangeable).

R$_f$ 0.50 silica gel 60 F254 chloroform:methylisobutylketone:acetic acid 50:50:1 A mixed melting point with a known sample of 4-(4-methoxyphenyl)-5-phenyl-2-oxazolepropanoic acid, the methyl ether of metabolite III of Janssen et al., gave m.p. 118°-120° C.

4-(4-Methoxyphenyl)-5-phenyl-2-oxazolepropanoic acid was demethylated as was the 5-isomer in Example 1. In this instance, after preparative High Pressure Liquid Chromatography, the isomer split was almost 1:1 as opposed to 2.5:1 in Example 1. Crystallized from 1:1 ethyl acetate:hexane; m.p. 184°–187° C.

IR 1680 cm$^{-1}$ s, 3270 cm$^{-1}$ (broad).

'H NMR (DMOS) $\delta$2.7–3.05 (2d, 4H), $\delta$6.75 (s, 1H), $\delta$6.8 (s, 1H), $\delta$7.3–7.65 (m, 7H), $\delta$9–10 (broad singlet, 1H exchangeable).

$R_f$ 0.47 silica gel 60 F254 CHCl$_3$:methylisobutylketone:acetic acid 50:50:1

Analysis for: $C_{18}H_{15}NO_4$ Calculated: C, 69.89; H, 4.89; N, 4.53. Found: C, 69.66; H, 5.02; N, 4.63.

A mixed melting point run with the 5-(4-hydroxyphenyl)-4-phenyl-2-oxazolepropanoic acid prepared in Example 1 gave m.p. 161°–170° C.

What is claimed is:

1. Crystalline 5-(4-hydroxyphenyl)-4-phenyl-2-oxazolepropanoic acid or a pharmaceutically acceptable salt thereof.

2. Chromatographically pure 5-(4-hydroxyphenyl)-4-phenyl-2-oxazolepropanoic acid or a pharmaceutically acceptable salt thereof.

3. A method for reducing inflammation in a mammal which comprises administering, orally or parenterally, an antiinflammatory amount of 4-(4-hydroxyphenyl)-5-phenyl-2-oxazolepropanoic acid, or 5-(4-hydroxyphenyl)-4-phenyl-2-oxazolepropanoic acid, or a pharmaceutically acceptable salt thereof, to a mammal in need thereof.

4. A method for reducing inflammation of claim 3 in which the antiinflammatory agent is 4-(4-hydroxyphenyl)-5-phenyl-2-oxazolepropanoic acid.

5. A method for reducing inflammation of claim 3 in which the antiinflammatory agent is 5-(4-hydroxyphenyl)-4-phenyl-2-oxazolepropanoic acid.

* * * * *